United States Patent
Panchal et al.

(10) Patent No.: US 10,294,914 B2
(45) Date of Patent: May 21, 2019

(54) HYDRAULIC INSTALLATION AND METHOD OF OPERATING SUCH AN INSTALLATION

(71) Applicant: ALSTOM RENEWABLE TECHNOLOGIES, Grenoble (FR)

(72) Inventors: Rajesh Panchal, Waghodia (IN); Nicholas Balcet, Sceaux (FR); Serge Prigent, Le Sappey en Chartreuse (FR)

(73) Assignee: GE RENEWABLE TECHNOLOGIES, Grenoble (FR)

( * ) Notice: Subject to any disclaimer, the term of this patent is extended or adjusted under 35 U.S.C. 154(b) by 70 days.

(21) Appl. No.: 15/305,192

(22) PCT Filed: Apr. 15, 2015

(86) PCT No.: PCT/EP2015/058169
§ 371 (c)(1),
(2) Date: Oct. 19, 2016

(87) PCT Pub. No.: WO2015/162043
PCT Pub. Date: Oct. 29, 2015

(65) Prior Publication Data
US 2017/0114768 A1    Apr. 27, 2017

(30) Foreign Application Priority Data
Apr. 23, 2014 (IN) .......................... 1105/DEL/2014

(51) Int. Cl.
*F03B 15/00* (2006.01)
*F03B 11/00* (2006.01)
(Continued)

(52) U.S. Cl.
CPC .......... *F03B 11/008* (2013.01); *F03B 11/004* (2013.01); *F03B 11/08* (2013.01);
(Continued)

(58) Field of Classification Search
CPC ........ E21B 47/06; G01M 15/08; G01L 23/10; G01N 15/06; G01N 2015/0053;
(Continued)

(56) References Cited

U.S. PATENT DOCUMENTS 4,316,386 A * 2/1982 Kerekes .................. E21B 23/02
166/318
6,152,684 A * 11/2000 Ferme ..................... F03B 11/04
415/1

(Continued)

FOREIGN PATENT DOCUMENTS

CN    102262106 A    11/2011
EP    1970561 A1 *    9/2008 ............ F03B 11/008
(Continued)

OTHER PUBLICATIONS

Machine translation of FR-2920542-A1 downloaded Dec. 13, 2018.*
(Continued)

*Primary Examiner* — Natalie Huls
*Assistant Examiner* — Mohammed E Keramet-Amircolai
(74) *Attorney, Agent, or Firm* — GE Global Patent Operation; Douglas D. Zhang

(57) ABSTRACT

The present invention relates to a hydraulic installation where sediment concentration in the water flow circulating through the cited installation is monitored continuously. According to the invention, the hydraulic installation comprises a pressure-reducing device and a primary sensor: the pressure reducing device decreases the pressure and discharge of upstream water flow, comprising sediments, allowing that the primary sensor can operate continuously measuring sediment concentration from the upstream water flow. The hydraulic installation also comprises a calibrating device, providing the primary sensor with a reference value
(Continued)

to be used for comparison matters and for establishing the content of sediment in the water flow.

18 Claims, 4 Drawing Sheets

(51) Int. Cl.
*F03B 11/08* (2006.01)
*F03B 13/08* (2006.01)
*F03B 15/06* (2006.01)
*G01N 15/06* (2006.01)

(52) U.S. Cl.
CPC .............. *F03B 13/08* (2013.01); *F03B 15/00* (2013.01); *F03B 15/06* (2013.01); *G01N 15/06* (2013.01); *F05B 2220/32* (2013.01); *F05B 2260/63* (2013.01); *F05B 2260/80* (2013.01); *Y02E 10/226* (2013.01)

(58) Field of Classification Search
CPC ....... F03B 11/008; F03B 11/004; F03B 11/08; F03B 15/06; F03B 13/08
USPC ................... 73/61.71, 61.78, 114.18, 152.51
See application file for complete search history.

(56) References Cited

U.S. PATENT DOCUMENTS

| | | | |
|---|---|---|---|
| 6,466,318 B1 | 10/2002 | Agrawal et al. | |
| 9,650,960 B2 * | 5/2017 | Vertenoeuil | F02C 7/232 |
| 2003/0066289 A1 * | 4/2003 | Watten | F03B 13/00 |
| | | | 60/398 |
| 2010/0013232 A1 * | 1/2010 | Prigent | B04C 1/00 |
| | | | 290/54 |
| 2011/0044824 A1 * | 2/2011 | Kelada | F03G 7/005 |
| | | | 417/53 |
| 2012/0117970 A1 * | 5/2012 | Ostlund | F04F 13/00 |
| | | | 60/660 |
| 2012/0267232 A1 * | 10/2012 | Riley | B01D 1/225 |
| | | | 203/11 |
| 2013/0019672 A1 * | 1/2013 | Hemsing | E21B 49/008 |
| | | | 73/152.51 |
| 2013/0082000 A1 * | 4/2013 | d'Artenay | B01D 61/025 |
| | | | 210/651 |
| 2013/0139494 A1 * | 6/2013 | Prigent | F03B 11/00 |
| | | | 60/325 |
| 2014/0037451 A1 * | 2/2014 | Oguma | F03B 3/06 |
| | | | 416/174 |
| 2014/0110494 A1 * | 4/2014 | Mills | B05B 5/025 |
| | | | 239/3 |
| 2014/0165571 A1 * | 6/2014 | Vertenoeuil | F02C 7/232 |
| | | | 60/734 |
| 2016/0046504 A1 * | 2/2016 | Riley | C02F 1/048 |
| | | | 203/11 |

FOREIGN PATENT DOCUMENTS

| | | | |
|---|---|---|---|
| FR | 2920542 A1 * | 3/2009 | ............ G01N 15/06 |
| JP | H094556 A | 1/1997 | |
| JP | 2007198388 A | 8/2007 | |

OTHER PUBLICATIONS

International Search Report and Written Opinion dated Oct. 29, 2015 which was issued in connection with PCT Patent Application No. PCT/EP2015/058169 which was filed on Apr. 15, 2015.
Machine translation and First Office Action and Search issued in connection with corresponding CN pplication No. 201580021143.3 dated Jun. 22, 2018.

* cited by examiner

HYDRAULIC INSTALLATION AND METHOD OF OPERATING SUCH AN INSTALLATION

TECHNICAL FIELD

Embodiments of the present invention relate to a hydraulic installation where sediment concentration in the water flow circulating through the cited installation is monitored continuously, and to a method for operating such a hydraulic installation.

BACKGROUND

In a hydraulic installation, where a forced flow of water passes through a hydraulic machine (of the type rotating turbine, pump or pump-turbine), the monitoring of sediment concentration in this water flow is of vital importance, as it originates abrasion phenomena in the hydraulic machine. In particular, sediment concentration is a key factor for hydro power projects that are located in rivers with high content of abrasive silt. As an example, the silt (sediment) content in a river flow during the flood season can go up from 100 mg/l to 10 g/l or even more. In spite of massive construction of de-silting basins provided, silt is moving ahead in the water flow; such high content of silt enters in the underwater hydraulic machine parts at significant speed of 20 m/s to 150 m/s, leading to severe abrasion and erosive wear in the cited hydraulic machine parts. Due to continuous impingement of silt onto the hydraulic machine parts being under water, erosion damages and changes the hydraulic profile of these underwater parts.

In order to mitigate this damage, abrasion resistant protection is applied on the hydraulic machine parts located under water, in order to enhance service hours. Moreover, at most of the sites, power plant operators shut down the hydraulic machine when a specific threshold silt concentration is reached. Hence, measuring the concentration of silt or sediment plays a significant role in the operation of a hydraulic machine.

At most of the hydraulic power plants, sediment concentration measurement in the flow is made by manual weighing of the flow passing through the machine comprising sediments, which is compared to a clean water sample used as reference. Although this method is reliable and accurate, it is also very cumbersome, time consuming, expensive, and the results are not available quickly, requiring very often weighing in order to provide a more continuous measurement of the sediment to establish a proper record.

It is known in the state of the art, as per U.S. Pat. No. 6,466,318 B1, for example, a device for measuring the diameter and area of particles in a given volume, by means of a submersible laser scattering instrument. A beam of laser light is directed across a void where a sample of water containing particles is admitted. After passing through the water, the light which is forward scattered out of the direct beam falls on two detectors at the same time, providing two measured outputs that, when electronically combined, give a mean diameter for the measured particles. However, such a system works on a sampling basis, which is not truly a continuous measurement. Moreover, this device can only work to a limit of 1000 mg/l: for higher concentration it may require dilution that may admit uncertainties in the measurement and a high pressure feeding of the system is not possible, as a local high water speed of erosive water would damage the system.

Therefore, it may be beneficial to develop a hydraulic installation where the measurement and monitoring of the sediment concentration in the water flow circulating through said hydraulic installation is done accurately and continuously.

Embodiments of the present invention are oriented towards providing such a hydraulic installation, and also to a method for operating such a hydraulic installation.

BRIEF DESCRIPTION

Embodiments of the present invention relate to a hydraulic installation where sediment concentration in the water flow circulating through the cited installation is monitored continuously.

According to an embodiment, the hydraulic installation comprises a pressure-reducing device and a primary sensor. The pressure reducing device decreases the pressure and discharge of upstream water flow, comprising sediments, allowing that the primary sensor can operate continuously measuring sediment concentration from the upstream water flow. The hydraulic installation also comprises a calibrating device, providing the primary sensor with a reference value to be used for comparison matters and for establishing the content of sediment in the water flow.

According to an embodiment, the hydraulic installation can also comprise at a barrage or a dam upstream river, a second sensor that also measures sediment concentration in the water flow at the barrage or dam, and a pump or second pressure-reducing device for the purpose of feeding properly the second sensor and a second calibrating device, aimed at transmitting an alarm signal to the turbine operator, in case the sediment concentration in the water flow raises a pre-defined limiting threshold value, well in advance for the operator to shut down the turbine operation.

The hydraulic installation can also comprise a third sensor, a second pump and a third calibrating device, installed typically downstream, at the outlet of the turbine, for measuring the sediment content in the downstream water flow just passed across the turbine.

Embodiments of the present invention also relate to a method of operating any of the hydraulic installations described above.

BRIEF DESCRIPTION OF DRAWINGS

The foregoing objects and many of the attendant advantages of the embodiments of the present invention will become more readily appreciated as the same becomes better understood by reference to the following detailed description when taken in conjunction with the accompanying drawings, wherein.

DETAILED DESCRIPTION

Figure 1:
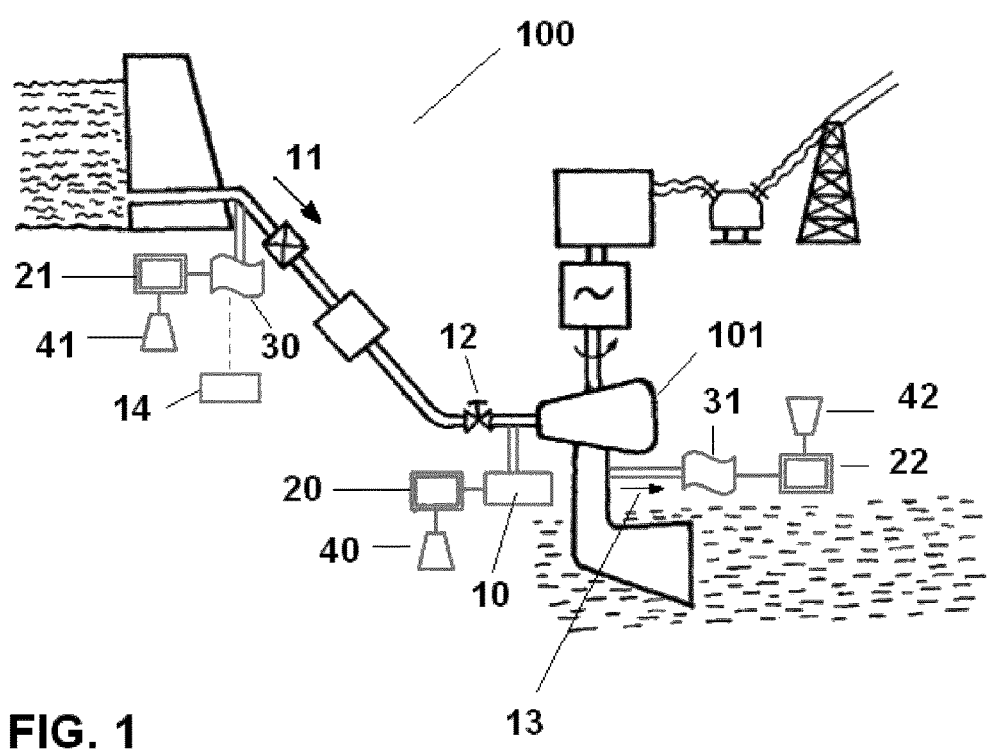
FIG. 1 shows an overall view of the hydraulic installation for sediment concentration monitoring in the water flow according to an embodiment.

According to an embodiment, the hydraulic installation 100 operating a hydraulic turbine 101 comprises a pressure-reducing device 10 and a primary sensor 20, as shown in FIG. 1. The pressure reducing device 10 creates significant hydraulic resistance and therefore decreases the pressure and discharge of upstream water flow 11, comprising sediments, allowing that the primary sensor 20 can operate continuously measuring sediment concentration in the upstream water flow 11. Depending upon the head available at different sites where the hydraulic installation 100 is going to work, the cited pressure-reducing device 10 is designed in such a way that it is able to decrease the relative pressure below 1 bar and discharge of the water flow 11 between 2 l/min to 8 l/min so that the primary sensor 20 can operate. In an embodiment, the location of the primary sensor 20 is close to the main inlet valve 12 at the turbine axis where full potential head is available, as shown in FIG. 1.

As shown in FIG. 1, the hydraulic installation 100 also comprises a primary calibrating device 40, providing the primary sensor 20 with the reference value (typically, from a sample of clean water) to be used for comparison matters and for establishing the content of sediment in the water flow 11.

With the installation of an embodiment of the invention, continuous recording of sediment concentration in the water flow 11 is done, due to the pressure-reducing device 10 allowing that the primary sensor 20 can work safely for turbine 101 with 10 m and up-to 2000 m head. This has been made possible by maintaining a low silted water velocity at desired pressure and flow for the sensor operation. The most important benefit may be that the hydraulic installation safeguards the sensor against severe abrasion normally begins with 30 m/s of water speed inclusive of 1 g/l abrasive silt content and permits the sensor to operate continually at highly abrasive sites for longer service period.

Figure 3:
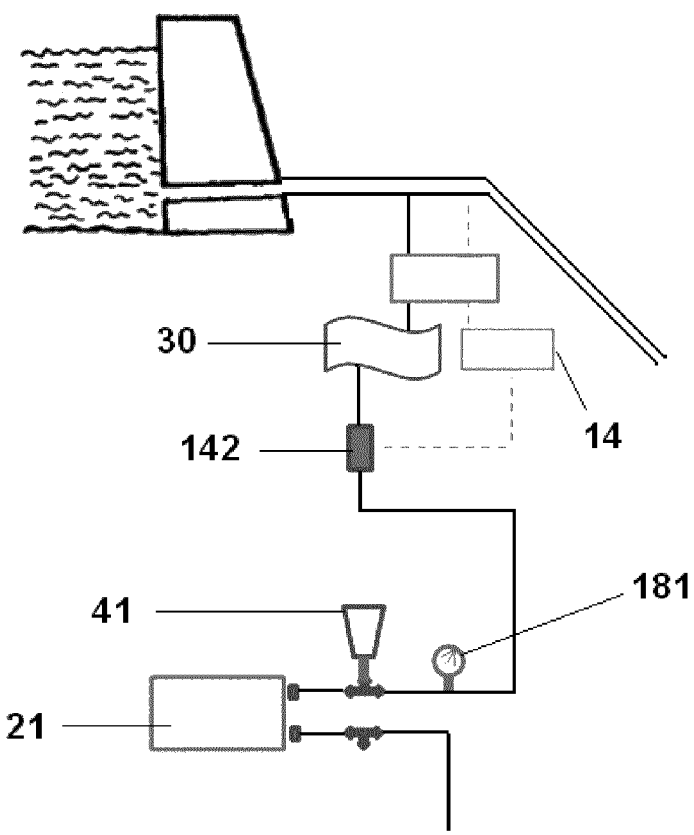
FIG. 3 shows the configuration of the upstream hydraulic installation for sediment concentration monitoring in the water flow according to an embodiment.

Further, according to an embodiment, the hydraulic installation 100 also comprises, at a barrage or a dam upstream river, a secondary sensor 21 that also measures sediment concentration in the water flow 11 at the barrage or dam. The hydraulic installation further includes a pump 30 or second pressure reducing device 14 and a second calibrating device 41 (see FIG. 1 or FIG. 3). The selection for installation of second pressure reducing device 14 or pump 30 will be based on site conditions with the objective to impart required flow and pressure at inlet of second sensor 21 to operate continuously. The purpose of the second sensor 21 is to transmit an alarm signal to the turbine operator, in case the sediment concentration in the water flow 11 raises a pre-defined limiting threshold value, well in advance for the operator to shut down the turbine operation.

In addition, the hydraulic installation 100 can also comprise a third sensor 22, a secondary pump 31 and a third calibrating device 42, installed typically downstream, at the outlet of the turbine 101, for measuring the sediment content in the downstream water flow 13, just passed across the turbine 101.

Figure 2:
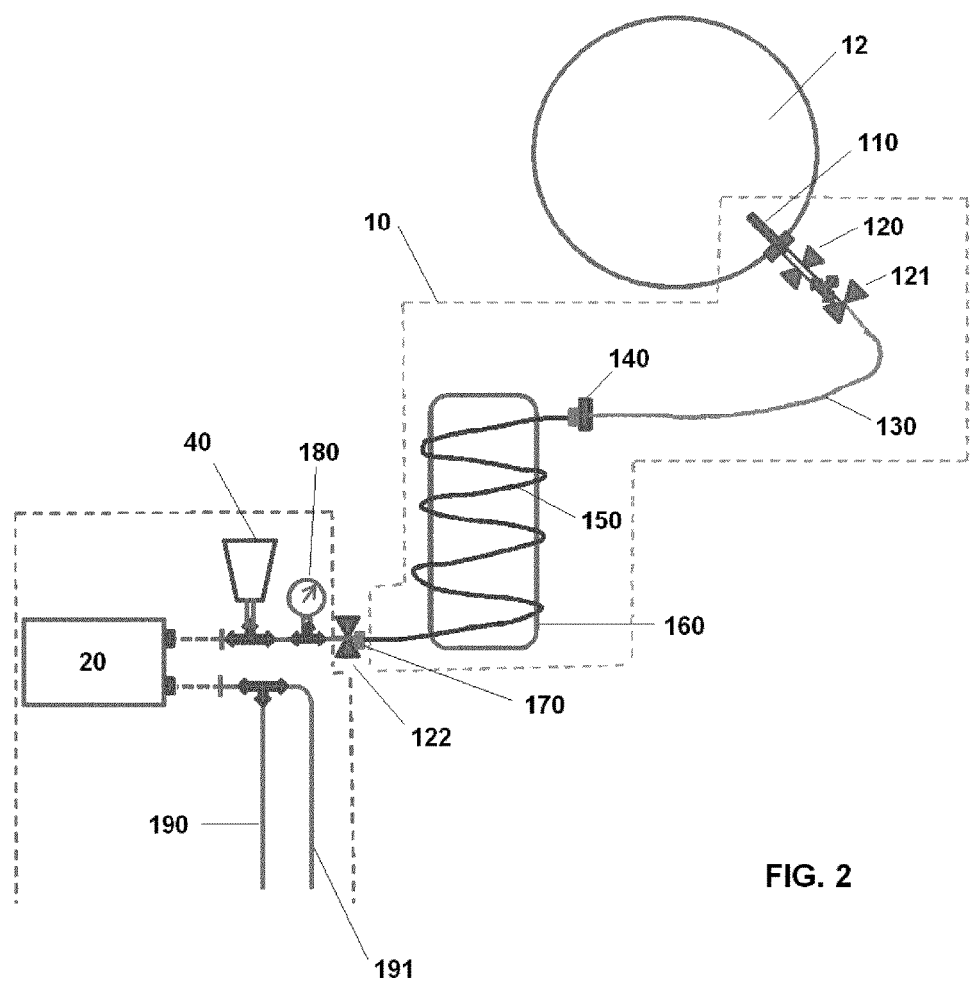
FIG. 2 shows the configuration of the pressure-reducing device in the hydraulic installation for sediment concentration monitoring in the water flow according to an embodiment.

FIG. 2 shows the components of the pressure-reducing device 10 and its installation connected to the primary sensor 20. A probe 110 is inserted to collect the water from the penstock line, typically through tapping. The probe 110 is designed in such a way that it will minimize the local transients and this is achieved by maintaining the probe entrance water speed close to the water flow speed in the penstock from 2 m/s to 15 m/s, thus collecting the water comprising sediments similar to which is moving towards the turbine 101.

The pressure-reducing device 10 also comprises at least two valves, first valve 120 and second valve 121, set just after the probe 110, having the objective to switch on the water flow to move forward in the pressure-reducing device 10; to provide emergency cut-off, and to conduct any maintenance work in the downstream line.

The pressure-reducing device 10 can also comprise more than two valves, and these would be used as spare valves for safety purpose in case of malfunctioning of the main valves first valve 120 and second valve 121.

Figure 4:
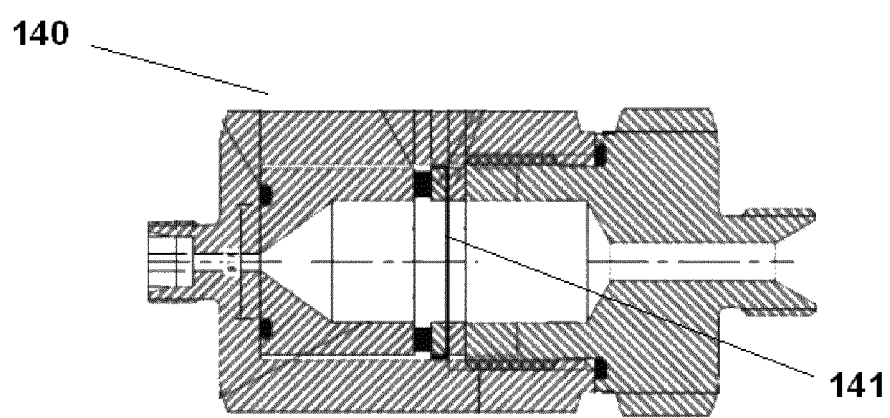
FIG. 4 shows a cross-section of the filter component of the pressure-reducing device in the hydraulic installation for sediment concentration monitoring in the water flow according to an embodiment.

A filter component 140 is added in the pressure-reducing device 10 in order to restrict the entrance of unwanted residues of cloth, rubber, thin sticks of wood or any other extraneous matter. Filter internal design encompasses a good hydraulic cross-section for smooth flow of water with sediments, as shown in representative example design in FIG. 4. The pore size 0.5 mm to 2 mm of the filter screen 141 is selected in such a way that it allows all the sediment particles to pass through except for big agglomerated matter as described above. For cleaning during major clogging of the filter component 140 and of the filter screen 141 over the period of time, separate spare filter screens 141 are provided for quick startup of the line. A high pressure flexible hydraulic hose 130 is used to connect the first and second valves 120, 121 to the filter component 140.

In an embodiment, after the filter component 140, a tubing 150, made of stainless steel, and having a spiral shape, is fitted, which is key segment of the whole pressure-reducing device 10 that offers significant hydraulic resistance to create major head loss. Preliminary loss coefficients are derived from the literature, and compared with actual water test: on receipt of appropriate loss coefficient, it is applied to any new project to define the characteristics of the tubing 150, mainly length and internal diameter.

A reference of the head loss values for a given discharge of 3.5 lpm is shown in Table 1 attached below.

TABLE 1

| | | HEAD LOSS $HL_f$ in meters - 3.5 LPM flow rate | | | | | | | | | |
|---|---|---|---|---|---|---|---|---|---|---|---|
| | | | | | | l (m) | | | | | |
| d (mm) | Velocity (m/s) | 2 | 3 | 5 | 8 | 10 | 12 | 14 | 16 | 18 | 20 |
| 2 | 18.6 | 439.3 | 658.9 | 1098.3 | 1757.2 | — | — | — | — | — | — |
| 2.5 | 11.9 | 146.8 | 220.2 | 367.1 | 587.3 | 734.2 | 881 | 1027.8 | 1174.6 | 1321.5 | 1468.3 |
| 3 | 8.3 | 59 | 90.2 | 150.4 | 240.6 | 300.8 | 361 | 421.2 | 481.3 | 541.5 | 601.6 |

TABLE 1-continued

HEAD LOSS $HL_f$ in meters - 3.5 LPM flow rate

| d (mm) | Velocity (m/s) | l (m) | | | | | | | | | |
|---|---|---|---|---|---|---|---|---|---|---|---|
| | | 2 | 3 | 5 | 8 | 10 | 12 | 14 | 16 | 18 | 20 |
| 3.5 | 6.1 | 28.9 | 43.4 | 72.3 | 115.6 | 144.5 | 173.4 | 202.3 | 231.2 | 260.1 | 289.1 |
| 4 | 4.6 | 15.1 | 22.6 | 37.7 | 60.4 | 75.5 | 90.6 | 105.7 | 120.8 | 135.9 | 151 |

Figure 5:
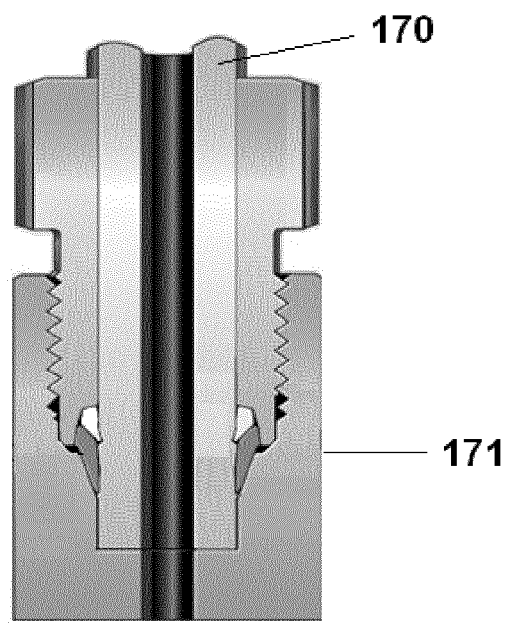
FIG. 5 shows a cross-section of the high pressure fittings in the tubing of the pressure-reducing device in the hydraulic installation for sediment concentration monitoring in the water flow according to an embodiment.

The tubing 150 is encircled in circular form like a spring, to occupy less space and to make it compact. The tubing 150 is supported by a suitable frame 160. Tubing ends 170 are affixed with special high pressure fittings 171 which ensure leak proof operation, as shown in FIG. 5: these fittings 171 are really simple to fix and open and, in case of little modification of the tubing 150, any tube joint can be easily introduced.

In the example design, a third valve 122 is fixed at down-stream of the tubing 150. The purpose of this third valve 122 is to bypass the flow in case of any malfunctioning of downstream line and to save the sensor 20 from high pressure damage.

A pressure gauge 180 is affixed at the inlet of the primary sensor 20 to read the pressure of the water flowing through. The pressure gauge 180 is mounted with a T-section fitting where its internal diameter is similar to the inside diameter of the sensor tubing.

The water flow 11 at high pressure gets adequate head loss while passing through the spiral tubing 150, and enters in the primary sensor 20 at required level of pressure with required range of water flow 11 for safe and erosion free operation. The primary sensor 20 measures the concentration of sediment in the water flow 11. The sensor can be based on either of working principle of ultrasound, time-of-flight, optics, laser, acoustic, conductivity, density, photo imaging, nuclear radiation or coriolis mass flow. Continual data of this sediment concentration is recorded and automatic post processing is made with software to register continuous sediment concentration readings. At the outlet of primary sensor 20, a sampling tube 190 is located, so that a water sample can be collected to cross-check the sediment concentration by manual sedimentation method, whenever needed.

Calibrating devices 40, 41 and 42 are used to verify the results of sensors 20, 21 & 22 as and when desired. This ensures the correct data with good level of accuracy all over the period. It is recommended to conduct in-situ verification of sensors at every three months after installation at project site.

It is to be understood that even though numerous characteristics and advantages of various embodiments have been set forth in the foregoing description, together with details of the structure and functions of various embodiments, this disclosure is illustrative only, and changes may be made in detail, especially in matters of structure and arrangement of parts within the principles of the embodiments to the full extent indicated by the broad general meaning of the terms in which the appended claims are expressed. It will be appreciated by those skilled in the art that the teachings disclosed herein can be applied to other systems without departing from the scope and spirit of the application.

What is claimed is:

1. A hydraulic installation for operating a hydraulic turbine, wherein sediment concentration in a water flow circulating through the installation is monitored, the hydraulic installation comprising:
   a pressure-reducing device; and
   a primary sensor,
   wherein the pressure-reducing device is designed to create hydraulic resistance with internal flow speed less than 15 m/s as a function of an operating head in the hydraulic turbine in such a way that the primary sensor can be operated continuously to measure sediment concentration in the water flow, and
   wherein the primary sensor is adaptable to face minimal effects of silt erosion and to augment service life.

2. The hydraulic installation according to claim 1, wherein a discharge of the water flow entering the primary sensor is flowing at a rate between 2 L/min and 8 L/min.

3. The hydraulic installation according to claim 2, wherein a downstream segment from a valve to an outlet line has a hydraulic resistance that is lower than the pressure-reducing device to ensure low pressure operation of the primary sensor below 1 bar relative pressure.

4. The hydraulic installation according to claim 1, wherein a downstream segment from a valve to an outlet line has a hydraulic resistance that is lower than the pressure-reducing device to ensure low pressure operation of the primary sensor below 1 bar relative pressure.

5. The hydraulic installation according to claim 1, further comprising a primary calibrating device, wherein the primary sensor is provided with a reference value to be used for comparison matters and for establishing a content of sediment in the water flow.

6. The hydraulic installation according to claim 1, wherein the operating head in the hydraulic turbine is between 10 m and 2000 m.

7. The hydraulic installation according to claim 1, wherein the primary sensor is proximate to a main inlet valve at an axis of the hydraulic turbine.

8. The hydraulic installation according to claim 1, further comprising:
   a second sensor configured to measure sediment concentration in the water flow at a barrage or a dam that is disposed upstream of the hydraulic turbine; and
   one of a pump or a second pressure reducing device, wherein the one of a pump or a second pressure reducing device is selected depending on site conditions to impart required flow and pressure at an inlet of the second sensor.

9. The hydraulic installation according to claim 8, further comprising a third sensor, a secondary pump and a calibrating device, wherein the third sensor, the secondary pump, and the calibrating device are all installed downstream at an outlet of the hydraulic turbine.

10. The hydraulic installation according to claim 9, wherein the pressure-reducing device comprises a filter component having a filter screen with a pore size between 0.5 mm and 2 mm.

11. The hydraulic installation according to claim 9, further comprising calibrating devices connected to the primary, secondary, and third sensors, respectively, wherein the calibrating devices are used to verify that the results of the sensor are consistent with predetermined values.

12. The hydraulic installation according to claim 11, wherein the sensors comprise ultrasound, time-of-flight, optics, laser, acoustic, conductivity, density, photo imaging, nuclear radiation, or coriolis mass flow sensors.

13. The hydraulic installation according to claim 11, wherein the sensors are configured to record continual data of sediment concentration in the water flow, and to output the continual data to a processor configured to automatically register continuous sediment concentration readings.

14. The hydraulic installation according to claim 1, wherein the pressure-reducing device comprises a probe configured to collect water from a penstock line at a similar speed to which the water flow is moving towards the hydraulic turbine.

15. The hydraulic installation according to claim 1, wherein the pressure-reducing device comprises a tubing having a length in the range of 0.3 m to 30 m and an internal diameter in the range of 1.5 mm to 5.5 mm.

16. The hydraulic installation according to claim 15, wherein the tubing has a spiral shape.

17. The hydraulic installation according to claim 1, wherein the second sensor is disposed upstream of the primary sensor.

18. The hydraulic installation according to claim 1, wherein the pressure-reducing device comprises a spiral-shaped tube.

* * * * *